United States Patent [19]

Storm

[11] 4,400,364

[45] Aug. 23, 1983

[54] PROCESS FOR OXIDIZING CARBON MONOXIDE IN THE PRESENCE OF METHACROLEIN

[75] Inventor: David A. Storm, Montvale, N.J.

[73] Assignee: The Halcon SD Group, Inc., New York, N.Y.

[21] Appl. No.: 284,155

[22] Filed: Jul. 17, 1981

[51] Int. Cl.³ .................. C07C 51/16; C01B 31/18; B01D 53/36

[52] U.S. Cl. .................. 423/247; 423/245; 423/437; 562/532

[58] Field of Search .............. 423/246, 247, 437; 562/532–535

[56] References Cited

U.S. PATENT DOCUMENTS

| | | | |
|---|---|---|---|
| 3,136,713 | 6/1964 | Miale et al. | 208/113 |
| 3,216,783 | 11/1965 | Cohn | 423/247 |
| 3,373,109 | 3/1968 | Frilette et al. | 252/455 |
| 3,373,110 | 3/1968 | Chen | 252/455 |
| 4,113,769 | 9/1978 | Padouan et al. | 562/534 |
| 4,174,459 | 11/1979 | Sakamoto et al. | 562/534 |
| 4,185,039 | 1/1980 | Eden | 423/247 |
| 4,238,460 | 12/1980 | Aiken et al. | 423/247 |
| 4,271,040 | 6/1981 | Khoobiar | 562/535 |
| 4,325,921 | 4/1982 | Aiken et al. | 423/247 |

FOREIGN PATENT DOCUMENTS 7602710 9/1976 Netherlands .................. 562/532

Primary Examiner—Gary P. Straub
Attorney, Agent, or Firm—William C. Long; Riggs T. Stewart; Harold N. Wells

[57] ABSTRACT

In a process for oxidation of methacrolein to methacrylic acid the carbon monoxide present in the recycle gas can be selectively oxidized to carbon dioxide with substantially no oxidation of the methacrolein content. A preferred catalyst for such an oxidation is a crystalline alumino silicate having pores of about 4–5 angstroms diameter and containing within the pores at least one metal or compound of the noble metal group, particularly platinum.

5 Claims, 1 Drawing Figure

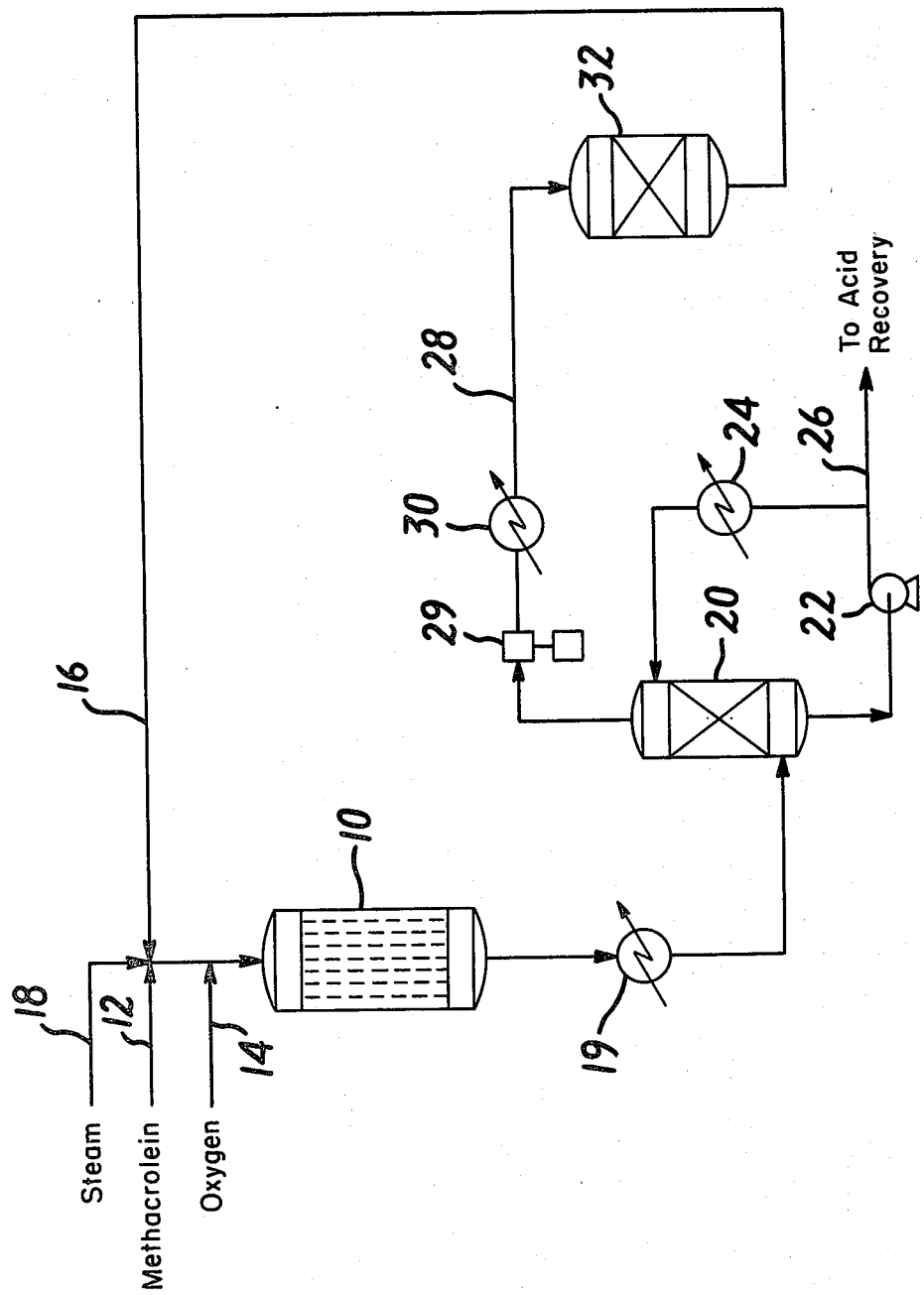

PROCESS FOR OXIDIZING CARBON MONOXIDE IN THE PRESENCE OF METHACROLEIN

PRIOR ART

This invention relates to the vapor phase oxidation of methacrolein to methacrylic acid. More particularly, it relates to a method for increasing the carbon dioxide content of the recycle gas, which would be used in practical applications of such an oxidation process.

The art contains many disclosures of process and catalysts directed to the oxidation of methacrolein by molecular oxygen to methacrylic acid in the presence of a suitable catalyst. Of particular interest with respect to the present invention is the process disclosed in U.S. Pat. No. 4,271,040. In a co-pending patent application, Ser. No. 284,156, filed July 17, 1981, it is disclosed that the performance of catalysts used for the oxidation of methacrolein to methacrylic acid can be enhanced by the increase in the carbon dioxide content of the feed gases. The contents of that co-pending application are incorporated herein by reference.

While the amount of carbon dioxide can be increased by directly adding it in once-through processes, in processes feeding substantially pure oxygen, it is typical to recycle unconverted methacrolein along with unreacted oxygen to the reactor. In such a case, carbon dioxide content of the recycle gas typically builds to a significant level, say about 30–40 vol %. Since carbon monoxide is also produced in about equal amounts relative to the carbon dioxide, it is also found present in large quantities in the recycle gas. In order to achieve the advantages of increased carbon dioxide in the feed gases, it is desirable to remove carbon monoxide, which has a detrimental effect on the oxidation of methacrolein. A preferred method of doing this is to oxidize carbon monoxide in the recycle gas to carbon dioxide. While the oxidation of carbon monoxide in itself is not difficult, the oxidation of methacrolein, which is also present in significant amounts, must be avoided. The present invention relates to a process for carrying out the oxidation of carbon monoxide to carbon dioxide in the recycle gases in such a manner that substantially no methacrolein is oxidized.

A selective oxidation process has been described in U.S. Pat. No. 3,136,713 in which it is mentioned that carbon monoxide can be selectively oxidized in the presence of branch chain hydrocarbons. No specific examples of such a process are given, but it is indicated that a characteristic of catalysts capable of carrying out such a selective oxidation is that they are capable of oxidizing normal paraffins, and in particular normal butanes, in the presence of isoparaffins, particularly isobutane. No mention is made of the oxidation of branched and unsaturated aldehydes such as methacrolein. It is necessary to oxidize methacrolein to methacrylic acid in the presence of a highly selective catalyst to avoid its oxidation to carbon dioxide and carbon monoxide. In the proposed reaction, it is desired to oxidize carbon monoxide in the presence of methacrolein. One skilled in the art would not be in a position to predict whether a selective oxidation of a carbon monoxide in the presence of methacrolein would be feasible.

With respect to catalyst found useful for this reaction, reference may be made to U.S. Pat. Nos. 3,373,109 and 3,373,110, disclosing crystalline alumino silicates prepared in such a way that an oxidation catalyst is placed within the pores of the alumino silicate and to which only small molecules have access, thus making possible the oxidation of only those molecules capable of penetrating the interior of the pores. The exterior surface of the catalyst is freed of oxidation catalyst and thus is relatively inert. It has now been found possible to adapt the type of catalyst previously disclosed to a new use in the oxidation of carbon monoxide to carbon dioxide in the presence of a stream containing methacrolein while substantially avoiding oxidation of methacrolein.

SUMMARY OF THE INVENTION

Carbon monoxide is selectively oxidized in preference to methacroleing in a gaseous mixture comprising carbon monoxide, carbon dioxide, oxygen, and methacrolein by passing the mixture over a catalyst under suitable oxidizing conditions, where the catalyst comprises a crystalline alumino silicate having pores no larger than about 4–5 angstroms diameter and containing substantially only within said pores at least one metal or compound thereof selected from the noble metal group. Preferably the catalyst contains platinum or a compound thereof in an amount up to about 1 weight percent, typically 0.005–0.5 weight percent based on the finished catalyst. The noble metal may be supplemented or even replaced by suitable base metals having the ability to oxidize carbon monoxide under conditions in which methacrolein is not oxidized.

Broadly, the gas mixture may comprise up to >0–80 vol % carbon oxides, >0–30 vol % oxygen, >0–10 vol % methacrolein, and >0–20 vol % water, plus inert gases and impurities. Typically, the gaseous mixture is the recycle gas of a process for the oxidation of methacrolein to methacrylic acid having a composition comprising about 60–70 vol % $CO_2$, 11–15 vol % CO, 6–10 vol % oxygen, 7–9 vol % steam, and 3–5 vol % methacrolein. The gas is passed over the catalyst at a temperature in the range of about 200°–350° C. at a suitable space velocity, typically about 1000–5000 GHSV, and the desired amount of the carbon monoxide present is oxidized to carbon dioxide, while substantially no methacrolein is burned to carbon oxides and water. Preferably, sufficient carbon monoxide is oxidized so that its buildup in the recycle gas is avoided.

BRIEF DESCRIPTION OF THE DRAWING

The sole FIGURE illustrates a process according to a preferred embodiment of the invention.

DESCRIPTION OF THE PREFERRED EMBODIMENTS

In the commonly-assigned application previously mentioned, it was shown that when oxidizing methacrolein to methacrylic acid an advantage is obtained if the ratio of carbon dioxide to carbon monoxide is greater than that produced by the oxidation reaction. Practically, this means that the $CO_2/CO$ ratio is changed by either adding carbon dioxide, removing carbon monoxide, or converting carbon monoxide to carbon dioxide.

The method selected will be affected by the form in which oxygen is supplied. There are two principal methods of providing oxygen needed for the oxidation of methacrolein, namely, as substantially pure oxygen or as air. Since conversion of methacrolein generally is less than one hundred percent, it is probable that any commercial plant will provide for separation of unconverted methacrolein and its recycle to the oxidation reactor. It will be recognized by those skilled in the art that such a choice is essentially an economic one in which the full usage of the valuable methacrolein is balanced against the costs of recycling.

In the typical situation, unreacted methacrolein will be recovered from the product methacrylic acid and recycled, along with other gases to the reactor. Where oxygen is supplied as air it is necessary to purge an amount of nitrogen equivalent to the amount fed and the concentration of nitrogen will equilibrate to a relatively high level, say about 60 volume percent of the recycle stream. Carbon oxides are produced by the combustion of some mathacrolein or other organic materials present in the oxidation reactor and will build up in the recycle stream until the amount purged with the nitrogen equals the amount of carbon oxides being produced. The total amount of carbon oxides in such a case will be relatively small, say 4–6 volume percent of the recycle gas.

An alternative and preferred mode of operation would be to supply the necessary oxygen as substantially pure oxygen and to recycle unconverted methacrolein, since only a small purge of gases is necessary. In such a situation, the carbon oxides build up and equilibrate at rather high concentrations, say about 60 volume percent of the recycle gas. While such an operation provides improved catalyst life and productivity as compared with a high concentration of nitrogen in the feed gas, it is the purpose of our invention to carry out the oxidation of methacrolein with more than the natural occurring ratio of carbon dioxide to carbon monoxide. While the molar ratio will vary depending upon the catalyst used and the operating conditions in the reactor, the natural ratio normally is found to be about 0.7/1 to 1.5/1. It may be adjusted by selectively oxidizing carbon monoxide to carbon dioxide, which is doubly beneficial, that is, the carbon monoxide concentration is reduced while the carbon dioxide level is increased. Such an oxidation may be carried out by contacting the recycle gas at a temperature of about 200°–350° C. with a suitable catalyst, which can carry out the oxidation without significantly oxidizing the methacrolein or other hydrocarbons present. Ideally, all of the carbon monoxide would be converted to carbon dioxide, but lesser amounts might be oxidized. Once a $CO_2$ ratio has been chosen, an amount of carbon monoxide at least equal to the amount made in each pass through the reactor must be oxidized to avoid a buildup of carbon monoxide.

According to a preferred embodiment of the invention, the recycle gas will be passed over a catalyst at a temperature of about 200°–350° C. to convert carbon monoxide to carbon dioxide with little or no methacrolein being burned to carbon oxides and water. It will be seen in the examples which follow that a selective oxidation catalyst suitable for this task is a crystalline alumino silicate having pores of about 4–5 angstroms, which pores contain a catalytic amount of at least one metal or compound selected from the noble metal group consisting of platinum, palladium, rhodium, and iridium. Other metals which have the ability to oxidize carbon monoxide and are capable of being deposited within the pores of molecular sieves of 4–5 angstrom diameter could be used to supplement or replace the noble metal(s). Examples of such base metals are silver, copper, nickel, iron, rhenium, vanadium, molybdenum, tungsten, and cobalt. The amount used will range up to about 1 weight percent based on the finished catalyst. Typically, the metal content will be from about 0.005 to 0.5 weight percent.

Such catalysts may be prepared by the methods disclosed in U.S. Pat. Nos. 3,733,109 and 3,373,110. The techniques described form crystals of alumino silicates in presence of a solution of the catalytic metal, thereby trapping the metal within the small pores. Any metal which remains on the accessible surfaces is removed by washing, ion-exchange or the like. As finished, the catalyst is presumed to have oxidation capability only within the small pores and can only oxidize those molecules which can gain access. However, will be seen in the examples, the catalyst may not be perfectly selective when operated under conditions suitable to the methacrolein oxidation process. Oxidation of both carbon monoxide and methacrolein have been observed, despite the fact that methacrolein molecules should be too large to enter the pores. Surprisingly, it has been found that when both carbon monoxide and methacrolein are present together, the desired objective is achieved, that is, only carbon monoxide can be oxidized with substantially no loss of methacrolein.

Ideally, a catalyst should be capable of oxidizing carbon monoxide to carbon dioxide while not burning methacrolein. The typical catalyst which is intended to oxidize methacrolein to methacrylic acid usually produces small amounts of carbon dioxide and carbon monoxide as it destroys a minor amount of methacrolein by combustion. When molecular oxygen is supplied in substantially pure form, it is economic to recycle unreacted methacrolein (about 60% is oxidized in each pass through the reactor), and unreacted oxygen (an excess above stoichiometric is supplied). Consequently, the carbon oxides build up in the recycle gas, typically up to about 40 vol % for each oxide. The typical recycle gas stream may contain about 3–5 vol % methacrolein, 6–10 vol % oxygen, 35–40 vol % $CO_2$, 35–45 vol % CO, 5–9 vol % steam plus some miscellaneous inert gases and oxidation by-products such as acetone, acetic acid, and formaldehyde. It is necessary to avoid burning of methacrolein while oxidizing the desired amount of carbon monoxide. The catalyst used can carry out such a selective oxidation, but surprisingly, only when both methacrolein and carbon monoxide are present, as will be seen in the following examples.

EXAMPLE 1

A selective oxidation catalyst was prepared by mixing 312 g of sodium aluminate in 1100 ml. deionized water and then adding 0.1504 g tetra amine platinous chloride in 70 ml. deionized water followed by 452 g of sodium metasilicate in 1100 ml. of deionized water. The mixed solutions were heated to 100° C. and refluxed for 6 hours. The resulting solids were filtered and washed with deionized water until the rinse water measured a pH=10. The solids were extruded to form ⅛" diameter catalyst pellets and dried in an oven for 3 hours at 80° C.

For each test described below, about 100 ml. of catalyst was charged to a ½ inch diameter (i.e.) reactor and the catalyst activated by passing air through the catalyst at 1000 GHSV and raising the temperature according to the following schedule:

200° to 250° C. over 2 hours
250° to 300° C. over 1 hour
300° to 350° C. over 1 hour
350° to 450° C. over 1 hour
held at 450° C. for 4 hours Following activation the temperature was lowered to the desired level and the tests carried out. The finished catalyst contained about 0.02 wt % platinum (by calculation).

EXAMPLE 2

A gas containing only 3–4 vol % methacrolein and 7 vol % oxygen (remainder nitrogen) is passed over catalyst prepared according to Example 1 at a temperature of 265° C. and at 0.7 kg/cm$^2$ gauge. At 2000 GHSV about 5% of the methacrolein is oxidized.

EXAMPLE 3

A gas containing about 3–4 vol % of methacrolein, 7 vol % oxygen, and 2 vol % carbon monoxide (remainder nitrogen) is passed over the catalyst of Example 2 at a temperature of 265° C. and 0.7 kg/cm$^2$ gauge. At 2000 GHSV about 20% of the carbon monoxide is oxidized to $CO_2$, while no measureable amount of methacrolein is found to have been oxidized.

The results of Examples 2 and 3 show that not only is the catalyst capable of doing the selective oxidation task required, but that if one were to test the catalyst for its inertness to methacrolein, one would not expect that this catalyst would be useful. It has been generally observed that above a temperature of about 350° C. methacrolein will be oxidized in large amounts, and below about 200° C., CO will not be oxidized significantly. Consequently, the existance of a range of temperatures within which only CO can be oxidized in the presence of methacrolein is unexpected.

The presence of methacrolein appears to affect the ability of the catalyst to oxidize CO also, as will be seen in the following example.

EXAMPLE 4

A gas containing about 12 vol % CO, 7 vol % $O_2$, and the balance nitrogen, is passed over catalyst prepared according to Example 1 at a temperature of 235° C. and at 0.7 kg/cm$^2$ gauge. About 11.4% of the CO is oxidized.

A gas having the same composition except that 4 vol % methacrolein was added is passed over the same catalyst at 235° C. and 0.7 kg/cm$^2$ gauge. About 5.2% of the CO is oxidized and none of the methacrolein.

It appears that the amount of CO oxidized to $CO_2$ is reduced by the presence of methacrolein. However, oxidation of only a portion of the carbon monoxide may be sufficient if it corresponds to the amount of carbon monoxide produced per pass during the oxidation of methacrolein to methacrylic acid. It is thus possible to adjust the absolute level of CO in the recycle gas, thereby achieving the desired level of carbon dioxide in the feed to the methacrolein oxidation reactor.

EXAMPLE 5

Catalysts are prepared according to the general method of Example 1 except that sufficient amounts of base metal are included to provide the following compositions.

| Wt. Percent | |
|---|---|
| Noble Metal | Base Metal |
| 0.05 Pd | — |
| 0.01 Pt | 0.1 Ni |
| 0.1 Pt, 0.1 Pd | — |
| none >0.1 Pd | 0.5 Ni |

| -continued | |
|---|---|
| Wt. Percent | |
| Noble Metal | Base Metal |
| none | 0.3 Cu |
| none | 1 Ag |

Each of the catalysts is used to oxidize carbon monoxide in gas streams having the compositions of Example 4.

The oxidation reaction may be carried out as shown in the figure in reactor 10, which may be of the tubular type, where the catalyst is formed into pellets and charged to the inside of vertical tubes which are surrounded on the outside by a heat transfer fluid such as the molten salts and special liquids typically used by those skilled in the art. Alternatively, other types of reactors could be used, provided that the heat released by the reaction is adequately removed. For purposes of this example oxygen is assumed to be substantially pure. Although no substantial purge of inerts is needed, it will be understood that a minor purge of inert gases would be likely in a commercial design, but this has not been shown in the simplified figure.

Fresh methacrolein is fed to the reactor 10 via line 12 and oxygen make up via line 14. These gases join the recycle stream 16 and mix before entering the reactor 10. The recycle stream 16 is substantially carbon dioxide, carbon monoxide, unreacted methacrolein, unreacted oxygen and steam, plus minor amounts of inert gases and light reaction by-products. The composition of the recycle stream 16 is about 67 volume percent carbon dioxide, 13 volume percent carbon monoxide, 4 volume percent methacrolein, 8 volume percent oxygen, and 7 volume percent steam plus 1 volume percent impurities. The amount of steam may be adjusted by control of the quench column 20 and if additional steam is needed it is added via line 18.

The combined feed gases to the oxidation reactor 10 has a composition as follows: 7 volume percent methacrolein, 12 volume percent oxygen, 20 volume percent steam, 50 volume percent carbon dioxide, 10 volume percent carbon monoxide, and 1 volume percent impurities. The temperature entering the reactor is about 280° C. It will be understood that the heat evolved is removed by circulating a heat transfer fluid (not shown) through the shell side of reactor 10 as is well known to those skilled in the art. The operating pressure is about 1.8 kg/cm$^2$ absolute.

The effluent gases pass through heat exchanger 19 for preliminary cooling and then enter quench tower 20 where they are cooled and condensed by countercurrent contact with a recirculating stream, which is substantially aqueous methacylic acid. The heat of condensation is removed by circulating the liquid via purge 22 through heat exchanger 24 and returning the liquid to quench tower 20. A portion of the liquid 26 is removed as stream 26 and sent to other facilities (not shown) for recovery of methacrylic acid. The uncondensed gases at a temperature of 40° C. are sent via compressor 29 and line 28 to carbon monoxide oxidation reactor 32. Depending upon the catalyst used, heat may be added in heat exchanger 30 (optional) to raise the gas temperature to the desired level. In this example, a fixed bed of 0.02 wt % platinum disposed in the pores of a molecular sieve is used in reactor 32, which is capable at a temperature of about 300° C. of converting about 10% of the carbon monoxide in the uncondensed gases leaving quench tower 20 to carbon dioxide. In a continuous equilibrated reaction system, the gases in line 28 will contain about 13 volume percent carbon monoxide and after the oxidation the gases in line 16 will contain about 11 volume percent carbon monoxide.

The amount of carbon monoxide converted to carbon dioxide will be controlled by the type and amount of catalyst used and the operating conditions. In order to avoid loss of methacrolein by oxidation the catalyst used must be capable of selectively oxidizing carbon monoxide to carbon dioxide without substantial oxidation of methacrolein. One such catalyst employs a noble metal oxidation catalyst such as platinum disposed within the pores of a molecular sieve having pores of 4–5 angstrom diameter. The pores of such sieves are too small to readily admit methacrolein to enter and be oxidized, but the smaller carbon monoxide molecules can be oxidized to carbon dioxide. Operation at a sufficiently low temperature permits the desired selective oxidation of carbon monoxide. It will be understood that the reaction conditions in reactor 32 would be established to convert an amount of carbon monoxide which produces an optimum effect on the performance of reactor 20 in accordance with the principles of our invention. This may be only so much carbon monoxide as is produced in each pass through the reactor or it may be more if it is desired to adjust the ratio of carbon dioxide to carbon monoxide.

What is claimed is:

1. A process for the selective vapor phase oxidation of carbon monoxide to carbon dioxide with molecular oxygen in the presence of methacrolein comprising passing a mixture comprising $>0-80$ vol % carbon oxides, $>0-30$ vol % oxygen, $>0-10$ vol % methacrolein, $>0-20$ vol % water and inert gases at a temperature within the range of about 200°–350° C. selected to oxidize carbon monoxide with substantially no loss of methacrolein over a catalyst comprising a crystalline alumino silicate having pores no larger than about 4–5 angstroms diameter and containing substantially only within said pores at least one noble metal or compound thereof of the group consisting of platinum, palladium, rhodium, and iridium.

2. A process of claim 1 wherein said noble metal is platinum.

3. A process of claim 1 wherein a base metal having the ability to oxidize carbon monoxide is added to said noble metal substantially only within said pores.

4. A process for the selective vapor phase oxidation of carbon monoxide to carbon dioxide with molecular oxygen in the presence of methacrolein comprising passing a mixture comprising $>0-80$ vol % carbon oxides, $>0-30$ vol % oxygen, $>0-10$ vol % methacrolein, $>0-20$ vol % water and inert gases at a temperature within the range of about 200°–350° C. selected to oxidize carbon monoxide with substantially no loss of methacrolein over a catalyst comprising a crystalline alumino silicate having pores no larger than about 4–5 angstroms diameter and containing substantially only within said pores a base metal having the ability to oxidize carbon monoxide.

5. A process of claims 1, 3 or 4 wherein said metals are present in an amount up to about 1 wt percent based on the finished catalyst.

* * * * *

UNITED STATES PATENT AND TRADEMARK OFFICE
CERTIFICATE OF CORRECTION

PATENT NO. : 4,400,364
DATED : August 23, 1983
INVENTOR(S) : David A. Storm

It is certified that error appears in the above-identified patent and that said Letters Patent are hereby corrected as shown below:

Column 2, line 13--change "methacroleing" to -- methacrolein --;

Column 4, line 60--change "(i.e.)" to -- (i.d.) --.

*Signed and Sealed this*

*Twelfth* Day of *March 1985*

[SEAL]

Attest:

DONALD J. QUIGG

*Attesting Officer*  *Acting Commissioner of Patents and Trademarks*